(12) United States Patent
Hoffman et al.

(10) Patent No.: US 9,531,156 B2
(45) Date of Patent: Dec. 27, 2016

(54) ENDOSCOPIC LIGHT SOURCE

(75) Inventors: David Hoffman, Santa Cruz, CA (US); Alexandr Ikriannikov, San Jose, CA (US)

(73) Assignee: Versatile Power, Inc., Campbell, CA (US)

( * ) Notice: Subject to any disclaimer, the term of this patent is extended or adjusted under 35 U.S.C. 154(b) by 444 days.

(21) Appl. No.: 12/487,591

(22) Filed: Jun. 18, 2009

(65) Prior Publication Data
US 2010/0228089 A1 Sep. 9, 2010

Related U.S. Application Data

(60) Provisional application No. 61/073,724, filed on Jun. 18, 2008, provisional application No. 61/181,962, filed on May 28, 2009.

(51) Int. Cl.
| | | |
|---|---|---|
| *H01S 5/042* | (2006.01) | |
| *H01S 5/062* | (2006.01) | |
| *A61B 1/06* | (2006.01) | |
| *A61B 1/07* | (2006.01) | |
| *H01S 5/068* | (2006.01) | |

(Continued)

(52) U.S. Cl.
CPC ........... *H01S 5/06213* (2013.01); *A61B 1/063* (2013.01); *A61B 1/0661* (2013.01); *A61B 1/07* (2013.01); *H01S 5/06216* (2013.01); *H01S 5/06808* (2013.01); *H01S 5/0014* (2013.01); *H01S 5/0427* (2013.01); *H01S 5/0428* (2013.01); *H01S 5/4025* (2013.01); *H01S 5/4087* (2013.01)

(58) Field of Classification Search
CPC .. H01S 5/0427; H01S 5/0428; H01S 5/06213; H01S 5/06216; H01S 5/06808; A61B 1/0661

USPC ............................................ 372/38.02, 38.07
See application file for complete search history.

(56) References Cited

U.S. PATENT DOCUMENTS

| | | |
|---|---|---|
| 4,011,403 A | 3/1977 | Epstein et al. |
| 5,408,998 A | 4/1995 | Mersch |

(Continued)

FOREIGN PATENT DOCUMENTS

| | | |
|---|---|---|
| WO | WO 95/20811 | 8/1995 |
| WO | WO 2005/009086 | 1/2005 |

OTHER PUBLICATIONS

Wong et al., "Tip of the week: How to best implement a synchronous buck converter"; EE Times design article, Apr. 26, 2008 (note first paragraph).*

(Continued)

*Primary Examiner* — Tod T Van Roy
(74) *Attorney, Agent, or Firm* — Terrence J. Edwards; TechLaw Ventures, PLLC

(57) ABSTRACT

A light source assembly includes multiple light emitters having output that are focused and mixed onto a optical fiber leading to an endoscope or other device. The emitters can be LEDs or solid state lasers that emit different colors. A driver circuit controls the relative output intensities of the light emitters so as to produce a desired light spectrum. A driver circuit includes a buck topology connected to a controller that provides current mode control. Pulse width modulation of the buck current is provided by a semiconductor switch across a solid state laser. A second order filter, formed by the an external inductor and the output capacitance of the buck topology, minimizes AC current ripple to the laser.

19 Claims, 11 Drawing Sheets

(51) Int. Cl.
*H01S 5/00* (2006.01)
*H01S 5/40* (2006.01)

(56) References Cited

U.S. PATENT DOCUMENTS

| | | | |
|---|---|---|---|
| 5,479,333 A * | 12/1995 | McCambridge et al. | 363/49 |
| 5,736,881 A | 4/1998 | Ortiz | |
| 5,748,657 A | 5/1998 | Gaddis | |
| 6,485,414 B1 | 11/2002 | Neuberger | |
| 6,987,787 B1 | 1/2006 | Mick | |
| 7,235,045 B2 | 6/2007 | Wang et al. | |
| 8,076,920 B1 * | 12/2011 | Melanson | 323/299 |
| 2003/0039280 A1 | 2/2003 | Mangano et al. | |
| 2005/0234302 A1 | 10/2005 | Mackinnon et al. | |
| 2005/0276291 A1 | 12/2005 | Nishimura | |
| 2006/0071639 A1 * | 4/2006 | Ross et al. | 320/116 |
| 2008/0224625 A1 * | 9/2008 | Greenfeld | 315/201 |
| 2009/0054957 A1 | 2/2009 | Shanbaky | |
| 2010/0164404 A1 * | 7/2010 | Shao et al. | 315/297 |

OTHER PUBLICATIONS

Microchip Inc., "Buck converter design example"; Microchip Web Seminar, 2006 (note slide 13).*

International Search Report for PCT/US2010/036740, mailed Aug. 10, 2010, 8 pgs.

Tymerski et al., "Generation, Classification and Analysis of Switched-Mode DC-to-DC Converters by the use of Converter Cells", Telecom. Energy Conference Int. IEEE, pp. 181-195, Oct. 1986.

* cited by examiner

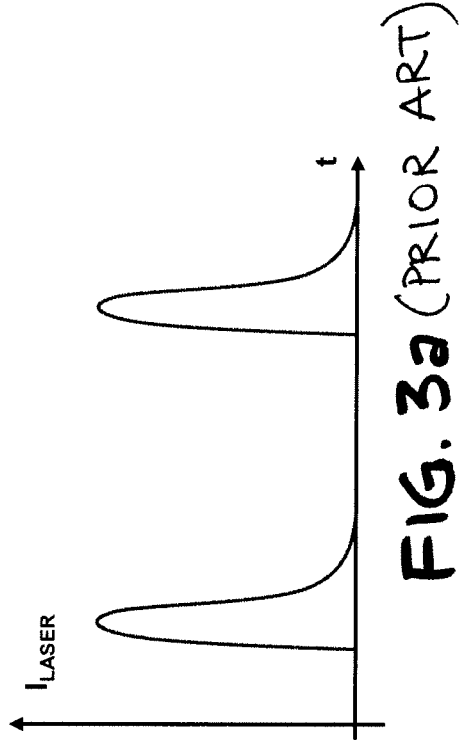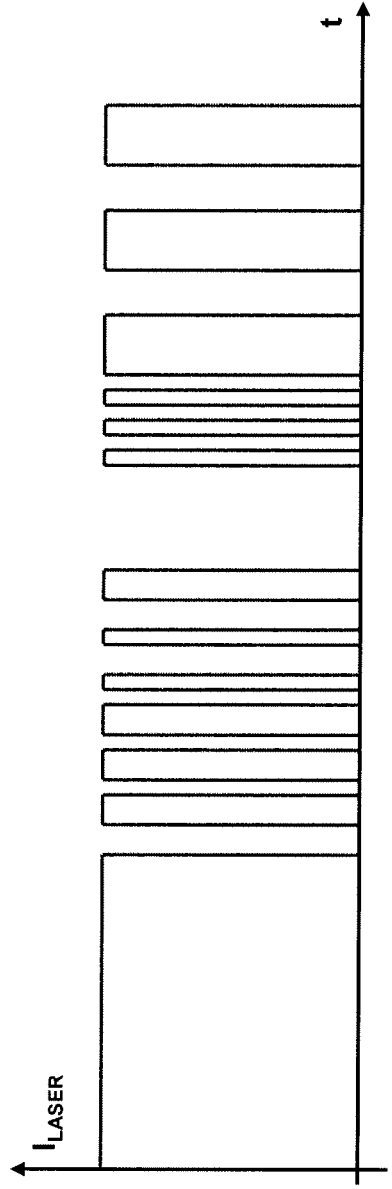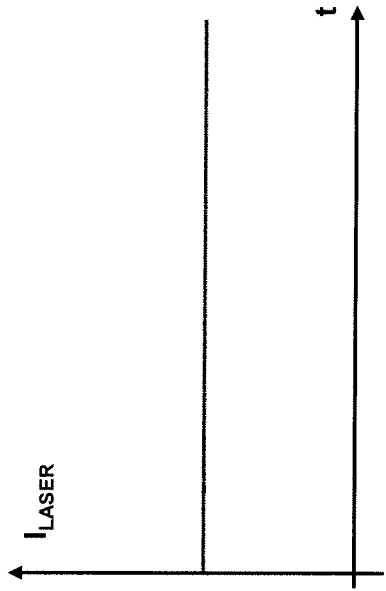

ENDOSCOPIC LIGHT SOURCE

This application claims the benefit of U.S. Provisional Application No. 61/073,724, filed Jun. 18, 2008, and U.S. Provisional Application No. 61/181,962, filed May 28, 2009, the entire contents of which are incorporated herein by reference.

FIELD OF THE INVENTION

This invention relates generally to a system and method for emitting light and, more particularly, to system and method for driving a solid state laser.

BACKGROUND OF THE INVENTION

In endoscopy, light is used in an area, such as within a human body cavity, that is remote from the actual light source. Xenon light sources have been used but xenon light bulbs are expensive, each costing hundreds to thousands of dollars. Also, xenon light bulbs require replacement every 300 to 500 hours, degrade in terms of light quality over time, and output a significant amount of infrared radiation that may cause unwanted heating of the tissue or object being viewed through the endoscope.

As an alternative to xenon bulbs, light emitting diodes (LEDs) may be used for their higher reliability, electrical efficiency, and color tunability through use of multiple LED colors. A problem with LEDs is that their light output is lambertian, or, more generally, diffuse in nature. Consequently, coupling of LED light output into a small diameter fiber optic of an endoscope is very inefficient and only a small percentage of the LED light output reaches the object to be viewed. Also, many LEDs must be used in an array to produce an equivalent amount or intensity of light as an incandescent or xenon bulb. Focusing the light from a multitude of LEDs in an array to a required spot at the end of a fiber optic cable is complicated and difficult. Multiple lenses would be required, one for each LED, with each lens focusing its own LED to the required spot. Also, fiber optics have a fixed numerical aperture, which is a dimensionless number that characterizes the range of angles over which the optical system can accept or emit light. As the angle of the light entering the optical fiber increases, the percentage of that light that is actually transmitted to the other end of the optical fiber decreases. These factors can make LEDs impractical for the high brightness output required for endoscopes which transmit light through optical fibers.

Lasers may be used as a light source for endoscopes as an alternative to xenon and LED emitters. However, lasers pose other challenges. Physical and electrical properties of semiconductor lasers, for example, require them to operate within fairly narrow bands of electrical current to maintain maximum light output and efficiency. With many types of lasers, the current level needed for maximum light output is beyond the level at which the lasers can be operated continuously without causing thermal damage to the lasers. To address this problem, a laser may be operated with pulses of current. For example, a laser that operates optimally at 60 amps (with a forward drop of 3 volts) but cannot dissipate more than 60 watts may be run at 60 amps for one third of the time. In addition to the aforementioned thermal issue, lasers are sensitive to the frequency at which the current is pulsed. If the current pulse frequency is too low, thermal issues and reduced efficiency result. If the current pulse frequency is too high, efficiency is also adversely affected.

Existing systems use a pulse width modulation (PWM) system to control power to the laser. With a PWM system, the "on" time of the current, or the "off" time of the current, is varied in order to control the percentage of time the current is supplied to the laser. The operating frequency is generally flexible and can be adapted to suite the particular laser being used. A problem with these existing PWM systems is that when implemented in an analog fashion (e.g., using a ramp and a comparator), the resulting accuracy and resolution of the output current to the laser is poor and does not lend itself to control by digital means. To avoid this problem, the PWM could be implemented in a fully digital system, but doing so to achieve high resolution requires a fast clock speed that, although possible, can be prohibitively expensive. For example, to achieve 4096 levels of resolution in the output current, with a typical 500 kHz operating frequency for a laser, would require a 2 GHz clock frequency (about 4096 multiplied by 500,000). Thus, such a fully digital approach limits the available devices for implementing the necessary logic and significantly increases cost compared to a lower frequency system.

Prior art systems 200 for controlling laser output have utilized a variable voltage source 202 that is switched off and on (for the pulsing) with a semiconductor 204 external to the voltage source and connected in series with the laser 206, as shown in FIG. 1. Such an approach results in poorly controlled current through the laser because the current from the voltage source is largely dependant on the load provided by the laser. The load provided by the laser varies as the laser heats and cools, as the laser ages, and due to other factors. Due to inherent variations within lasers, the load also varies from laser to laser. The variation in load causes the current to the laser to vary, making it difficult to maintain load current at levels that produces optimal laser light output.

Another laser driver design 300, as shown in FIG. 2 and disclosed in U.S. Pat. No. 5,748,657 entitled "High Efficiency Constant Current Laser Driver, incorporated herein by reference, has been developed to support constant output current to a laser 302. However, such a design 300 cannot support transient or pulsing output to the laser. Current to the laser is constant, as shown in FIG. 2a. A common buck topology is formed by switches 304 and 306, an inductor 308, and an output capacitance 310. Such a system 300 allows for current mode control. The large output capacitance 310 is used at the buck converter output to conduct inductor AC current ripple, ensuring constant voltage, with very small voltage ripple, at the buck converter output to the laser diode 302. The result is almost constant load current into the laser diode 302. The current into the laser diode 302 is sensed and controlled by adjusting the output voltage of the buck converter. As previously mentioned, transient or pulsing of load current, which is often required for optimal optical output of solid state lasers, is not supported by such a design.

Other prior art systems 400, such as shown in FIG. 3 and often used for driving high power lasers, support pulsing. However, as shown in FIG. 3a, the shape of the load current pulse is not an ideal square wave and is defined by exponentials associated with capacitive discharge, and current level is not constant (has a curved peak) during the pulse. A regulated DC rail (Vdc) is created by the DC/DC converter 402, which may be a buck converter or full bridge. An energy storage capacitor 404 is charged to Vdc via resistors 406, 408, limiting the charge current. A clamp diode 410 provides a charging path and ensures that the laser diode 412 does not develop high voltage above a level that would cause breakdown during reverse biasing. When a switch 414, typically a MOSFET (metal oxide semiconductor field effect transistor), is turned on (closed state), the storage capacitor 40 discharges through the switch, causing a current pulse in the laser diode 412. The resistor 408 limits the amplitude of the current pulse. Another resistor 416 allows current sensing of the pulse amplitude. The combination of the resistance value of the resistor 408, Vdc amplitude, and duration that the switch 414 is turned on allows the amplitude and duration of the current pulse to be adjusted. That is, pulse duration or duty cycle is dependant on circuit values. With this circuit, current is not constant during the pulse, as previously mentioned. The circuit is difficult to control and adjust, and typically cannot be controlled dynamically without risking damage to the laser. Also, as charging and discharging of the energy storage capacitor 404 is done via resistors in a linear fashion, significant power loss in the circuit is unavoidable. Additionally, when the switch 414 is turned on and the system delivers the current pulse to the laser by discharging capacitor 404, during which resistor 406 simply dissipates power from Vdc without any useful function as it is effectively shorted across Vdc by switch 414.

Accordingly, there is a need for a light source for endoscopic use and other uses that is cost efficient, energy efficient, reliable, and provides color tunability. There is also a need for a driver circuit that allows for cost efficient, accurate, and precise load current for a light emitter.

SUMMARY OF THE INVENTION

Briefly and in general terms, the present invention is directed to a light emitting system that comprises an electrical current source outputting an output current, at least one solid state laser adapted to received the output current and emit light, and a digital controller configured to change the output current to the laser in a manner that changes the intensity from of the emitted light. In some aspects of the invention, the system further comprises a semiconductor switch electrically connected in parallel to the laser. The switch adapted to periodically activate and deactivate to pulse the output current to the laser at a pulse frequency and a pulse width. A controller may be used to modulate the pulse frequency and pulse width. In some aspects of the invention, the system comprises a plurality of solid state lasers, each one of the solid state lasers outputting light that is mixed together in an output optical fiber. In further aspects, the system further comprises an endoscope optically coupled to a distal end of the output optical fiber. In detailed aspects, the plurality of solid state lasers includes a first laser configured to output red light, a second laser configured to output green light, and a third laser configured to output blue light. In other aspects, lasers with additional colors could be added to address desired output spectrum of the system, including lasers with wavelengths outside of the range visible to the human eye.

In other aspects of the invention, a method of emitting light comprises providing electrical current to a plurality of solid state laser devices that produce light at a different spectrum from each other, the provided current having a peak or average level that is independent of temperature-induced variations of the electrical load provided by the laser device, the current having a pulse waveform defined by a pulse frequency and duty cycle. The method also comprises mixing the light produced by each one of the laser devices, and adjusting the intensity of the light produced by at least one of the laser devices, the adjusting including at least one of changing the peak or average level, the pulse frequency, and the duty cycle of the current provided to the at least one of the laser devices. In some aspects, adjusting the intensity includes changing the pulse frequency or pulse width through control of a semiconductor switch adapted to short the laser. In further aspects, providing the current is performed at least by a buck topology that includes a power source electrically connected to a series buck switch, a parallel buck switch, a buck inductor and an output capacitance, the buck switches being transistor devices.

The features and advantages of the invention will be more readily understood from the following detailed description which should be read in conjunction with the accompanying drawings.

BRIEF DESCRIPTION OF THE DRAWINGS

FIG. 2*a* is a plot of the current to a laser provided by the driver of FIG. 2.

FIG. 3*a* is a plot of the current to a laser provided by the driver of FIG. 3.

FIG. 10*a* is a plot of the current to a laser provided by the drive circuit of FIG. 10.

DETAILED DESCRIPTION OF PREFERRED EMBODIMENTS OF THE INVENTION

Figure 4:
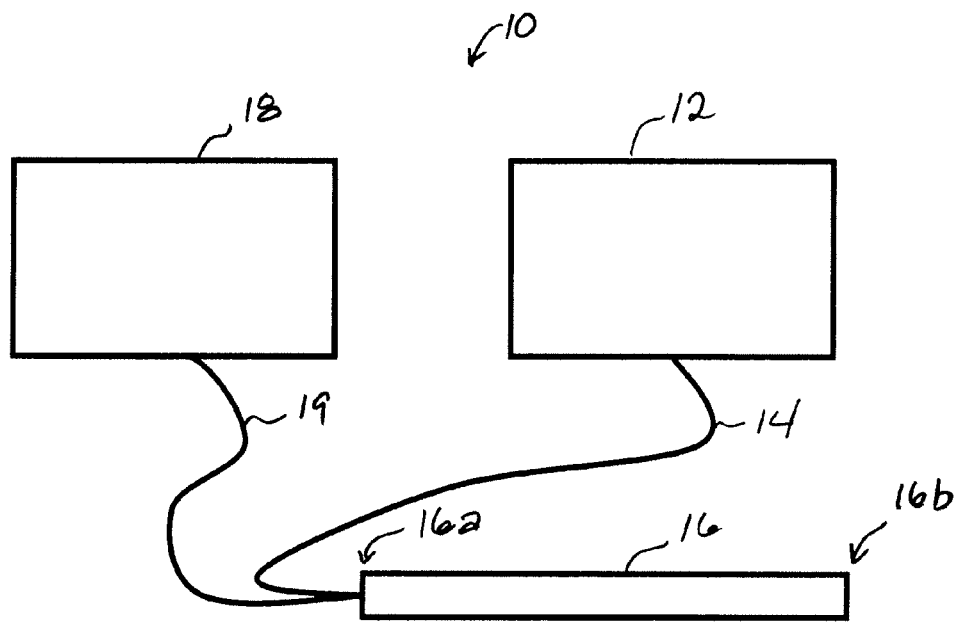
FIG. 4 is a diagram of a system for providing light to an endoscope, showing a light source assembly connected to the endoscope by a fiber optic cable, and a viewer for displaying images of tissues and objects in front of the endoscope.

Referring now in more detail to the exemplary drawings for purposes of illustrating embodiments of the invention, wherein like reference numerals designate corresponding or like elements among the several views, there is shown in FIG. 4 a system 10 for providing light to an endoscope. A light source assembly 12 is connected by a fiber optic bundle or cable 14 to an endoscope 16. The fiber optic cable 14 can be connected to and disconnected from the light source assembly 12. The fiber optic cable 14 may be an integral part of the endoscope 16 or may be considered a separate part that can be connected to and disconnected from the endoscope. The endoscope 16 is adapted to enter a human or animal body and can have a rigid or flexible tube structure.

The light source assembly 12 includes one or more light emitters and circuitry for controlling the light emitter(s). Light emitted from the light emitter is transmitted through the fiber optic cable 14 where it enters a proximal end 16a of the endoscope and is outputted or emitted out of a distal end 16b of the endoscope. As used herein, "distal" is used to describe an element or structure that it located toward the tissue or object being viewed or illuminated, and "proximal" is used to describe an element or structure that is located toward the light emitter. A camera or lens system at the distal end 16b of the endoscope captures or receives an image that is illuminated by the emitted light and transmits the image to a viewer 18 that includes a video screen that displays the received image. Electrical or optical signals representative of the image are communicated by a cable 19 to the viewer 18. The endoscope may include one or more lumen or channels that allow entry of medical instruments into the human or animal body.

In some embodiments, the light source assembly 12 can include an array of three light sources. Each light source can be a single light emitter. Alternatively or in combination, the light sources can include multiple light emitters arranged in a subarray. The light emitters can output different colors or different visible and/or non-visible electromagnetic radiation spectra which are combined to generate light having a broad spectrum that is delivered to and out of the endoscope 16.

The light emitters can be LEDs or lasers. Preferably, though not necessarily, the light emitters include a red laser configured to emit red light, a green laser configured to emit green light, and a blue laser configured to emit blue light. The light emissions or output from the individual lasers are mixed and focused within the light source assembly 12 prior to delivery to the endoscope 16.

Figure 5:
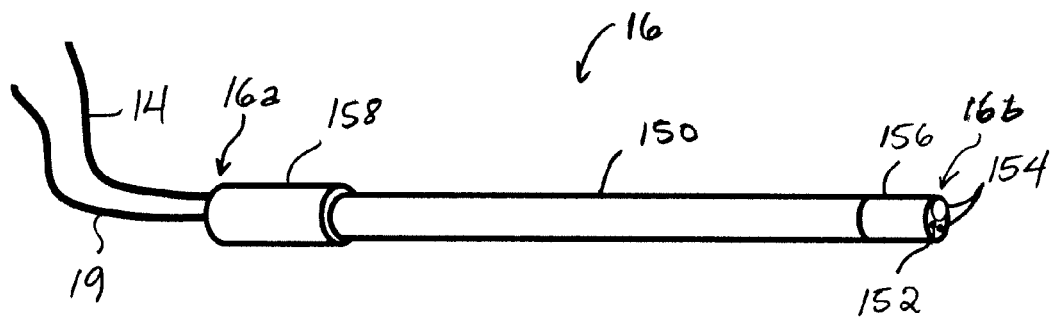
FIG. 5 is a perspective view of an endoscope.

The endoscope 16 can be used in a variety of medical procedures in which imaging of a body tissue, organ, cavity or lumen is required. The types of procedures include, for example, arthroscopy, bronchoscopy, colonoscopy, laparoscopy, and sigmoidoscopy. In some embodiments, as shown in FIG. 5, the endoscope 16 includes an insertion tube 150 having a light output port 152 and two longitudinal channels 154. In use, the light output port 152 is optically coupled to the fiber optic cable 14 so that it emits light produced by the light source assembly 12. In general, however, the insertion tube 150 may have any number of longitudinal channels. At least one of the longitudinal channels 154 is sized to receive an instrument that can reach into a body cavity to perform a desired procedure, such as taking a biopsy or performing a polypectomy. The instrument may be, for example, a retractable needle for drug injection, scissors, clamps, grasping tools, knives, electrocoagulation systems, ultrasound transducers, electrical sensors, heating elements, and other means of ablation. In some embodiments, one of the channels 154 can be adapted to supply an irrigation liquid or to supply an insufflation gas, such as carbon dioxide, as may be desired during a surgical procedure. The channels 154 may also be used to extract fluids or inject fluids, such as a drug in a liquid carrier, into the body.

Still referring to FIG. 5, the insertion tube 150 is steerable or has a steerable distal end region 156. The length of the distal end region 156 may be any suitable fraction of the length of the insertion tube 150, such as one half, one third, or one tenth. The insertion tube 150 may have control cables within it. One end of the control cables may be anchored at or near the distal end 16b of the insertion tube 150. The other end of the control cables are attached to controls in the handle 158, enabling the wires to be pulled so as to bend or articulate the distal end region 156 of the insertion tube 150 in different directions as desired by the user. The handle 158 of the endoscope 16 may have one or more ports and valves for controlling access to the channels 154 of the insertion tube 150.

In other embodiments, the endoscope 16 in the system 10 is replaced by a laparoscopy light source, a laparoscopy camera, an ophthalmic light source, a pipe inspection tool, or other device. Such devices may be for consumer or industrial use, and may be adapted to deliver light or capture images in remote or confined spaces.

Figure 6:
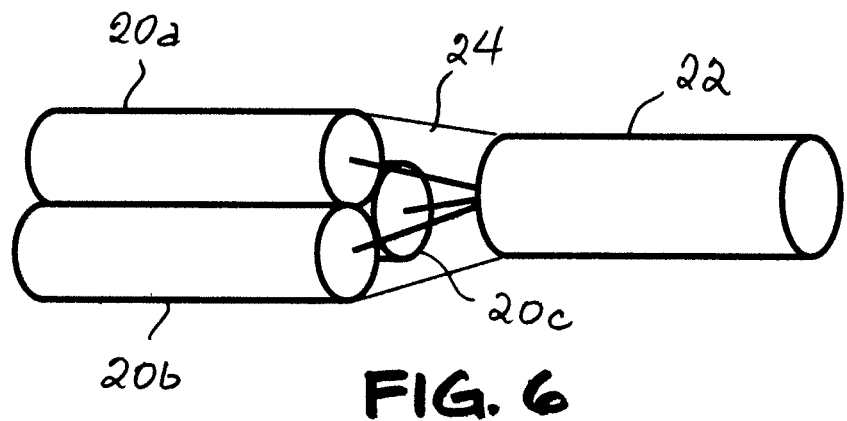
FIG. 6 is a perspective view of supply optical fibers from different lasers optically coupled by a fused junction to an output optical fiber that carries light to an endoscope or other device.

As shown in FIG. 6, output from light emitters, which can be LEDs or lasers, in the light source assembly 12 can be transmitted through separate optical fibers 20a, 20b, 20c, each having a diameter at or about 800 microns. Optical fibers, which can be made of glass or plastic, are adapted to carry light along its length. Light is kept in the core of an optical fiber by internal reflection. It will be appreciated that fibers having other diameters may be implemented as needed depending on the type, number, and arrangement of light emitters in the light source assembly 12.

In some embodiments, a first supply optical fiber 20a transmits red light from a red laser, a second supply optical fiber 20b transmits green light from a green laser, and a supply third optical fiber 20c transmits blue light from a blue laser. The supply optical fibers are arranged so that their light output are mixed and focused within the light source assembly 12 prior to delivery to the endoscope 16. The light output can be mixed by fusing or welding the distal ends of the supply optical fibers, after the ends have been stripped of cladding, to the proximal end of an output optical fiber 22 which has also been stripped of cladding. The output optical fiber 22 can have a diameter at or about 1000 microns, though other diameters may be used depending on the number and diameter of the supply optical fibers.

Fusing or welding of the distal ends of the supply output fibers 20a, 20b, 20c to the distal end of the output optical fiber 22 can be performed with the aid of a fixture that allows the operator to observe and adjust the output of the supply optical fibers before or during the fusing process to maximize the light throughput or level of light transmission from the supply optical fibers to the output optical fiber. The fusing or welding creates a fused junction 24 that is attached between the distal ends of the supply optical fibers and the proximal end of the output optical fiber. The fused junction 24 focuses and mixes the output from supply output fibers 20a, 20b, 20c onto to small spot on the distal end of the output optical fiber 22. The fused junction 24 can be placed in a package or housing to give it mechanical strength.

The proximal ends of the supply optical fibers 20a, 20b, 20c are optically coupled to the lasers using a separate lens for each laser/fiber pair. As used herein, "optically coupled," means that visible and non-visible light output from one element, such as one of the lasers, is transmitted to and received by another element, such as one of the supply optical fibers. Non-visible light includes electromagnetic radiation in the infrared and ultraviolet spectrum range.

The output optical fiber 22 may be two to seven meters in length and may be coiled inside the enclosure or housing of the light source assembly 12. The coils or loops cause multiple reflections to mix the light carried in the output optical fiber 22 so as to create a homogenous color output at the distal end of the output optical fiber. The distal end of the output optical fiber 22 is coupled to an outlet port of the light source assembly enclosure, which allows the output optical fiber 22 to be connected to and transmit the homogeneously mixed light to the fiber optic cable 14 of the endoscope 16.

Figure 7:
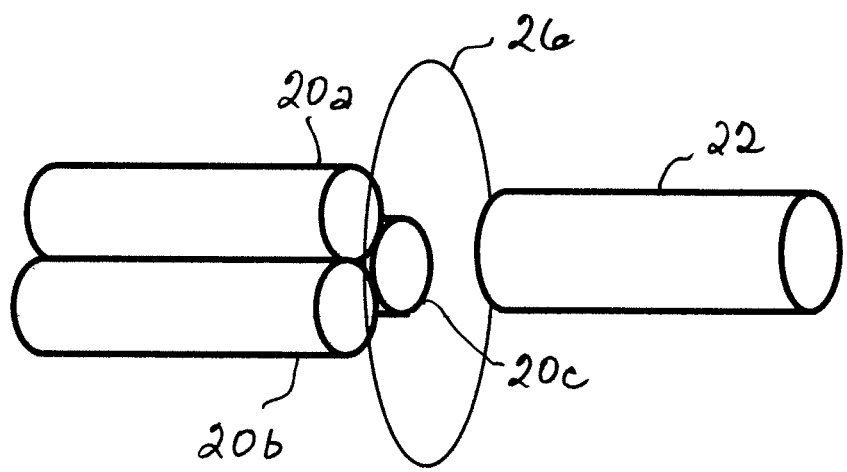
FIG. 7 is a perspective view of supply optical fibers from different lasers optically coupled by lens to an output optical fiber that carries light to an endoscope or other device.

As shown in FIG. 7, light from the lasers can be mixed by an optical lens 26 disposed between the distal ends of the supply optical fibers 20a, 20b, 20c and the proximal end of the output optical fiber 22. The lens 26 optically couples the supply optical fibers 20a, 20b, 20c to the output optical fiber 22 and is configured to mix and focus light output from the distal ends of supply optical fibers onto the proximal end of the output optical fiber.

In FIGS. 6 and 7, the distal ends of the supply output fibers 20a, 20b, 20c are shown substantially parallel to each other. In some embodiments, the distal ends are arranged at slight angles, depending on the optical coupling method implemented, to facilitate focusing of the light output onto the proximal end of the output optical fiber 22.

Figure 8:
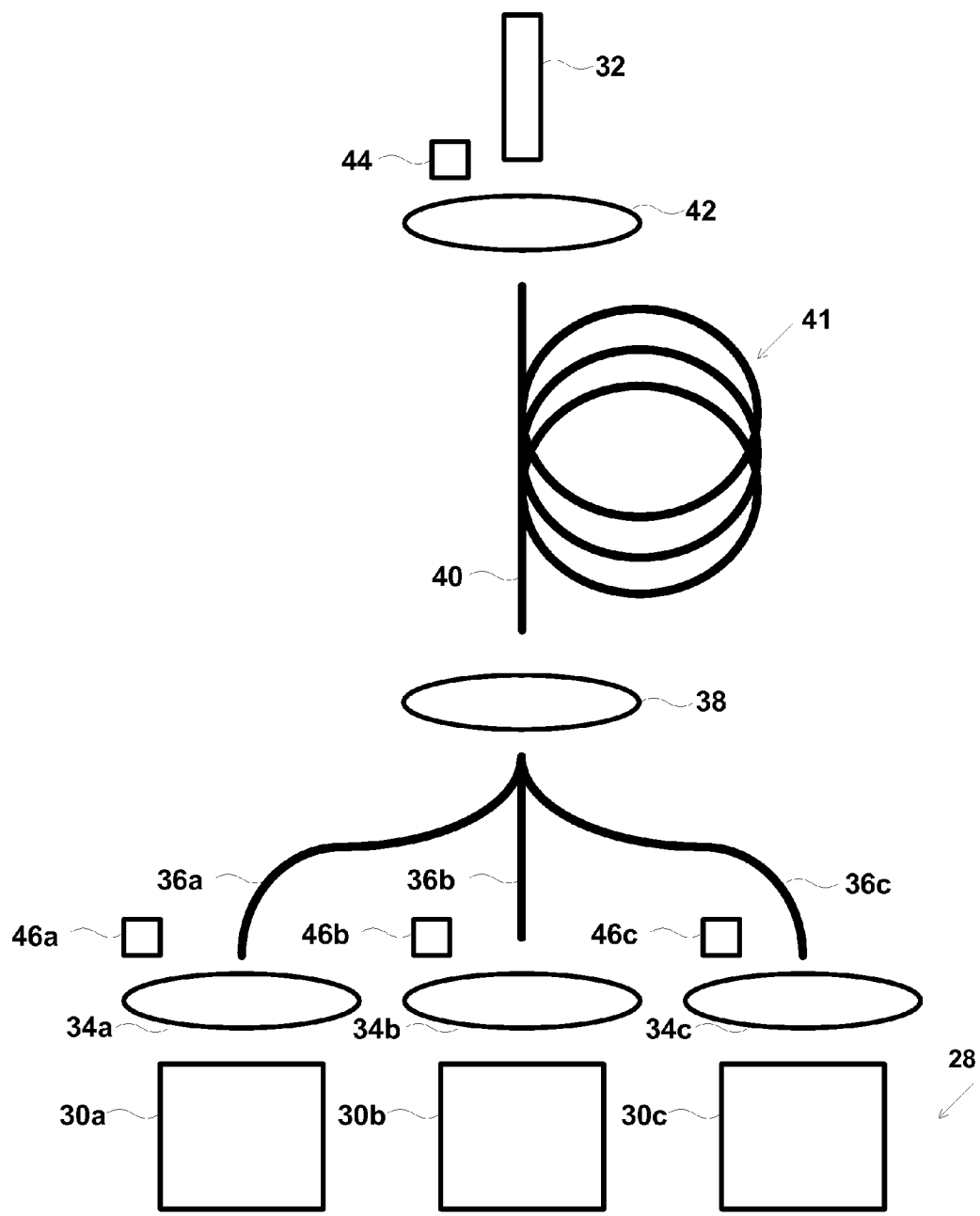
FIG. 8 is a diagram of an array of light sources optically coupled to a fiber bundle by lenses located between the light sources and the fiber bundle, the fiber bundle carrying light to an endoscope or other device.

Referring next to FIG. 8, an array 28 of three light sources 30a, 30b, 30c can be optically coupled to a fiber bundle 32 to an endoscope, or other device, by a plurality of lenses. The light sources includes individual light emitters, which can be LEDs or lasers. There can be one light emitter in each light source, or there can be multiple light emitters in each light source.

In some embodiments, the light sources 30a, 30b, 30c each include at least one laser. A first set of lenses 34a, 34b, 34c can be used to couple each laser to the input end of a supply optical fiber 36, which can be 800 microns in diameter in some embodiments. The output ends of the supply optical fibers 36a, 36b, 36c are coupled to an output optical fiber 40 by a mixing lens 38. The mixing lens 38 is configured to mix the light output of the supply optical fibers and focus the mixed light to the input end of the output optical fiber 40. The output optical fiber 40 may be coiled to form one or more loops 41 that produce internal reflections within the output optical fiber to mix the light carried therein and, thereby, create a homogenous color output at the output end of the output optical fiber. At the output end of the output optical fiber 40 there is an output lens 42 that optically couples the output optical fiber to the fiber bundle 32 to the endoscope.

In other embodiments, the fiber bundle 32 is connected to a laparoscopy light source, a laparoscopy camera, an ophthalmic light source, an industrial inspection tool, or other device.

In some embodiments, the light source array 28 includes three lasers that can be configured to provide different types of light. In some embodiments, one of the three lasers provides a red light spectrum, another laser provides a green light spectrum, and yet another laser provides a blue light spectrum. The red, green, and blue spectra are mixed together to provide white light or other desired spectrum of light to an endoscope or other device.

In other embodiments, the light source array 28 can include less than three lasers or more than three lasers. In some embodiments, a light source array may include two or more lasers that provide light having the same color spectrum. For example, all the lasers in the array may be configured to output red light having the same spectrum or a slightly different spectrum. The spectrum of light provided to the endoscope by the light source array 28 can be adjusted as desired by varying the relative intensity of the individual lasers in the array. Varying the relative intensities of lasers of different colors allows for the creation of a very wide range of colors, including white, and mixtures of visible light and non-visible light. Non-visible light can include infrared light, ultraviolet light, or both.

As used herein, "intensity" of a laser or other light emitter means optical power or energy delivered by the electromagnetic radiation outputted by the light emitter. Intensity includes visible and non-visible wavelengths. The term "brightness" refers to the intensity of the visible component of the outputted electromagnetic radiation. For lasers and other light emitters, output intensity is proportion to input power or current.

A single color of light may not provide optimum contrast and visibility for all situations in a particular application. In medical applications, blue or green light may be the optimal color to best show the capillaries, and red light may be the best color to enhance the visibility of veins. An array with different color lasers allows colors to be changed very rapidly, as desired, without having to connect the endoscope to a different light source. Thus, it will be appreciated that fine control of the color mixture would enable a surgeon or other user of the endoscope to enhance definition of anatomic features according to need.

A light source array may, in some embodiments, include a source of visible light and a source of infrared light and/or ultraviolet light. Some wavelengths in the infrared range are able to penetrate tissue up to several centimeters. Cameras coupled to the endoscope can be configured to be sensitive to infrared wavelengths to enable a surgeon to see through tissue to locate bone or blood vessels. That is, the camera is configured to make the infrared light visible so that when it passes through tissue, underlying structures such as bone and/or blood vessels become visible to the surgeon. In addition, light in the ultraviolet range is associated with different luminescence of different matter and tissues. The difference is detected in the re-emitted or reflected wavelengths, time and intensity of the re-radiation. This would allow for differentiation of different cells and tissues during an endoscopic or other medical procedure.

Referring again to FIG. 8, each one of the light sources 30a, 30b, 30c of the array 28 may include multiple lasers. In some embodiments, the first light source 30a is a group or subarray of lasers with output combined into a small point by a lens 34a in front of the lasers. The second and third light sources 30b, 30c are configured similarly to the first light source 30a, each with their own group or subarray of lasers and focusing lenses 34b, 34c in front of the lasers. Each subarray 30a, 30b, 30c can include 10 lasers so that the entire array 28 has 30 individual lasers. The lasers within the same subarray can have the same color so that the first, second, and third light sources can output red, green, and blue light respectively, which are subsequently focused together by the mixing lens 38. Each of the lasers in each subarray can have its own speckle pattern. The speckle patterns combine to produce an output with much less perceivable speckle.

In some embodiments, the array 28 delivers light to the endoscope that has a non-visible and visible component. A camera for capturing an image of an illuminated tissue or object can then be configured to respond to the non-visible infrared light so as to become more sensitive to visible light.

Thus, sensitivity of the camera to visible light can be improved by including an infrared source in the light source array.

Referring once again to FIG. 8, a light sensor 44 provides optical feedback to a driver circuit to allow for automatic adjustment of color temperature to compensate for aging or temperature-induced drift in color. The light sensor 44 may be located adjacent the lens 42 that couples the output optical fiber 40 to the fiber bundle 32. The lens 42 directs some of the homogenously mixed light to the sensor 44. By detecting color, the light sensor 44, may be adapted to allow selection of color temperature of the white light output to achieve better contrast. Cavities or flat surfaces of tissues may require illumination by different color temperatures for optimal contrast and resolution. Also, making the white light output spectrum cooler (i.e., shift towards blue) could induce an observer to increase his mental concentration and visual focus, while making the white light spectrum warmer (i.e., shift towards red) could help the observer relax so as create less visual strain over the duration of a prolonged surgical procedure. The light sensor 44 can be an RGB sensor that is configured to detect individual intensities of red, green and blue components of the mixed light output. Electrical signals from the light sensor 44 which are representative of color intensities is communicated to a processor, such as in a current controller or PWM controller, that will be able to adjust the intensities of the red, green and blue light emitters in the array, as needed.

In some embodiments, separate light sensors 46a, 46b, 46c are located adjacent the lenses 34a, 34b, 34c directly in front of the light sources 30a, 30b, 30c. The lenses 34a, 34b, 34c direct some of the focused light from the light sources to their respective light sensors 46a, 46b, 46c. The sensors 46a, 46b, 46c can be connected to a processor, such as in a current controller or PWM controller, which controls driver circuits for light emitters. In this way, feedback from the light sensors 46a, 46b, 46c to the driver circuits, in addition to or as an alternative to the feedback provided by the light sensor 44 for mixed light, can be used to calibrate light output to compensate for color temperature drift or to achieve a desired color temperature selected by a physician or other user.

The output of the lasers in a light source array can be controlled using a combined scheme of pulse width modulation and modulation of current level. The combined scheme allows for very accurate control at relatively low cost. Applicants' study of efficiency curves of lasers has shown that there is a narrow band of currents through which the efficiency of the laser will remain somewhat constant. Efficiency, in this case, means output light power divided by input electrical power.

In one embodiment, a light emitter utilizing NECSEL (TM) technology, which is a semiconductor laser technology platform manufactured by Necsel of Sunnyvale, Calif., was used. The particular NECSEL device is a solid state laser array, scaled for approximately 3 watts of total optical output. The NECSEL device was found by Applicants to operate at nearly the same efficiency over a current band of 57 to 63 amps (referred to as a "predetermined band"), some brightness adjustment of the light output could be performed by varying the current supplied to the laser within the predetermined band. An inexpensive 8-bit digital to analog controller can be used to provide 256 levels of current within the predetermined band (i.e., 57-63 amp window). A pulse width modulation (PWM) circuit with 16 levels of resolution can be implemented in combination with the digital to analog controller to provide a laser light output control resolution of 4096 levels. Thus, the 4096 levels of control for a laser with a typical 500 kHz operating frequency would require a clock frequency as low as 8 MHz (16 multiplied by 500,000), as compared to 2 GHz in prior art approaches discussed in the Background section above. The lower clock frequency of 8 MHz is much easier and less expensive to implement than higher frequencies.

The lasers in a light source array can be solid state lasers, which is a gain medium that is a solid (such as a crystalline solid), as opposed to a liquid or a gas. Suitable examples of solid state lasers include, without limitation, devices manufactured by Sony, Mitsubishi, and Necsel. Solid state lasers can only produce maximum output when pulsed within a narrow range of frequencies, a narrow range of pulse widths, and a narrow range or band of current levels. To obtain maximum light output to an endoscope 16, the control circuitry for the solid state lasers in a light source assembly 12 may be configured to control all three of the variables, namely pulse frequency, pulse width, and current level. A range for each of the pulse frequency, the pulse width, and the current level can be determined to enable simultaneous control of two or more of the variables to obtain a wider operating range of output intensity while maintaining optimal efficiency of the laser device.

In other embodiments, the light emitters in a light source array are LEDs. For example, the light sources 30a, 30b, 30c in FIG. 8 can each be a subarray of high intensity LEDs. The first light source 30a can be a subarray of LEDs with output combined into a small spot by the lens 34a in front of the LEDs. The second and third light sources 30b, 30c can be configured similarly to the first light source 30a, each with their respective subarray of LEDs and focusing lenses 34b, 34c. Each subarray 30a, 30b, 30c can include any number of LEDs. The LEDs within the same subarray can have the same color so that the first, second, and third light sources can separately output red, green, and blue light, respectively, which are subsequently focused together by the mixing lens 38. Within each subarray, the LEDs may be connected in series and have the same current. The current for each subarray of LEDs may be driven by separate drive circuits adapted to provide separate and independent control of red, green, and blue light components of the mixed light delivered to the fiber bundle 32.

In some embodiments of the present invention which have lasers as light emitters, each laser can be driven by separate drive circuits within the light source assembly 12 (FIG. 4). The laser drive circuits may be adapted to provide separate and independent control of red, green, and blue light components of the mixed light delivered to the fiber bundle 32.

Figure 1:
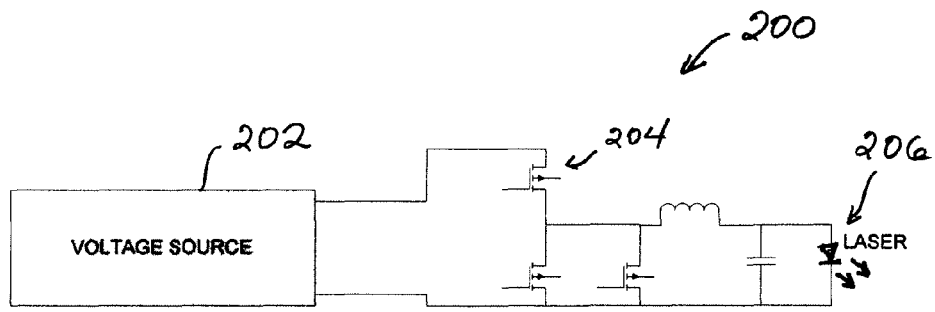
FIGS. 1, 2, and 3 are diagrams of prior art drivers for lasers.
Figure 9:
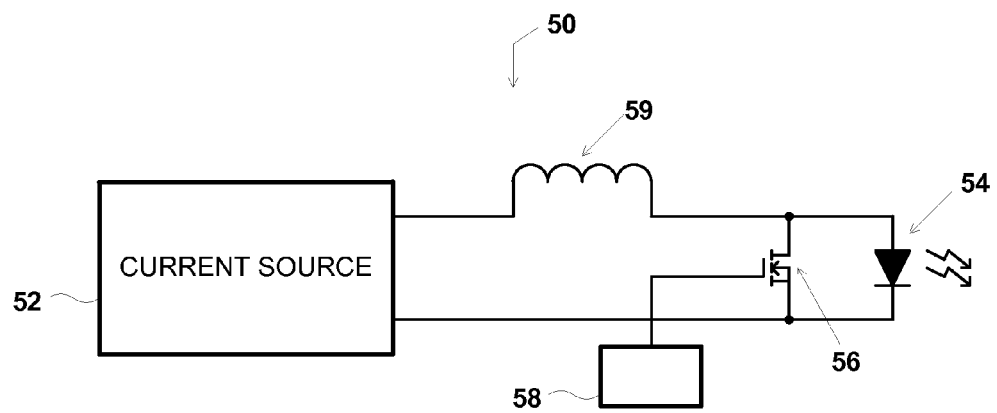
FIG. 9 is a diagram of a drive circuit for a laser light source, showing an adjustable current source and a chopper across a laser.

In some embodiments, as shown in FIG. 9, a drive circuit 50 includes an adjustable current source 52. An advantage of the adjustable current source 52 over the prior art shown in FIG. 1 is that the current through the laser 54 will always be the same regardless of inherent variations in the load provided the laser due to heating and cooling of the laser, age of the laser, and other factors. Another advantage is that pulsing of the laser can be done with a semiconductor 56, referred to as a chopper, connected in parallel or across with the laser. The current source 52 may be controlled by an 8-bit digital-to-analog controller to provide 256 levels of current within a range that has been predetermined to produce optimal light output from the laser 54.

The semiconductor 56 opens, then closes to short out the laser 54. The semiconductor 56 effectively pulses the current load to the laser, causing the laser to turn off and on very rapidly and accurately. In prior art systems with voltage sources, such as shown in FIG. 1, shorting a laser with a semiconductor or other device arranged in parallel to the laser would either damage the power supply or cause a very high current to flow across the semiconductor upon closing due to discharge of the capacitor across the laser. When the semiconductor is subsequently opened, the high current would have to charge the capacitor across the laser first, with slew rate limited by inductor, causing extreme delay in turning on the laser.

Driving the laser 54 as described above allows for modulation or adjustment of the intensity of the laser that is more accurate over prior art systems. By driving the laser with a current source, as opposed to a voltage source, current to the laser can be varied linearly, which in turn linearly varies the output intensity of the laser. Accurate control of the pulsing of the laser by the semiconductor 56 across (parallel to) the laser also allows for more accurate control of the output intensity. Combining accurate current control and accurate pulse width control allows the drive circuit to operate over a narrower range of current and pulse width, which allows laser efficiency to be maximized while still achieving the required intensity modulation.

Referring again to FIG. 9, a PWM controller 58, which may include one or more microcontrollers. The PWM controller 58 is shown in block diagram form and operatively connected to the switching semiconductor 56. The PWM controller is adapted to activate and deactivate the semiconductor 58 and to control the frequency at which the semiconductor activates and deactivates and to control the time duration that the semiconductor is activated and deactivated. Activation of the semiconductor 56 corresponds to the closed switch state, which shorts the laser 54 and effectively prevents current from the current source 52 and inductor 59 from reaching the laser 54. Deactivation of the semiconductor 56 corresponds to an open switch state, which allows current from the current source 52 and the inductor 59 to reach the laser 54. The frequency at which the semiconductor activates and deactivates corresponds to the current pulse frequency to the laser. The fraction of time that the semiconductor 56 is deactivated corresponds to the current duty cycle.

The controller 58 may be configured to provide 16 levels of resolution in the laser output intensity, which in combination with an 8-bit digital-to-analog controller for the current source 52, provides a resolution of 4096 levels of laser output intensity. With a pulse frequency of 500 kHz, the controller 58 would then need to have a clock frequency of at least 8 Mhz.

Figure 10:
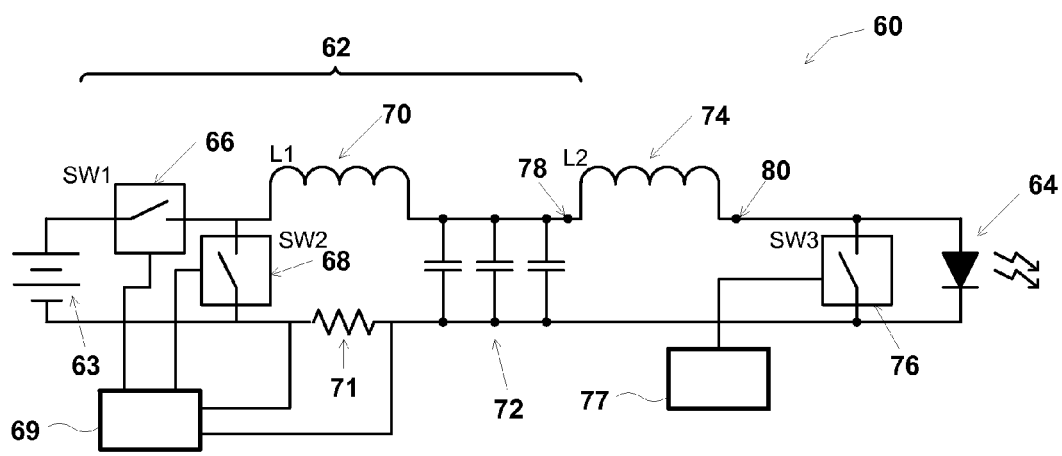
FIG. 10 is a diagram of a drive circuit for a laser light source, showing a buck converter output connected to an output inductor having an output connected to a chopper disposed across a laser.

In some embodiments, as shown in FIG. 10, a drive circuit 60 in the light source assembly 12 includes a buck converter 62, which is a step-down DC-to-DC converter, that provides a source of current to a solid state laser 64. The buck converter 62 includes a DC power source 63, which could be created from the standard AC power distribution lines, connected to a series switch 66, a parallel switch 68, a buck inductor 70, and an output capacitance 72. The buck switches 66, 68 can be MOSFETs, bipolar transistors, or other devices adapted to electronically controlled to allow for switching rates of up to tens of megahertz. Switching rates include without limitation 10 MHz, 20 MHz, 30 MHz, and 40 MHz. It will be appreciated that other switching rates may be implemented. In the illustrated embodiment of FIG. 10, the buck switches 66, 68 are not diodes. The switches 66, 68 operate to alternatively provide current to the buck inductor 70 to store energy in the buck inductor 70 during the buck on state, and discharge the buck inductor 70 to the laser load during the buck off state. The buck on state corresponds to when the series switch 66 is closed and parallel switch 68 is open. The buck off state corresponds to when the series switch 66 is open and the parallel switch 68 is closed.

Figure 2:
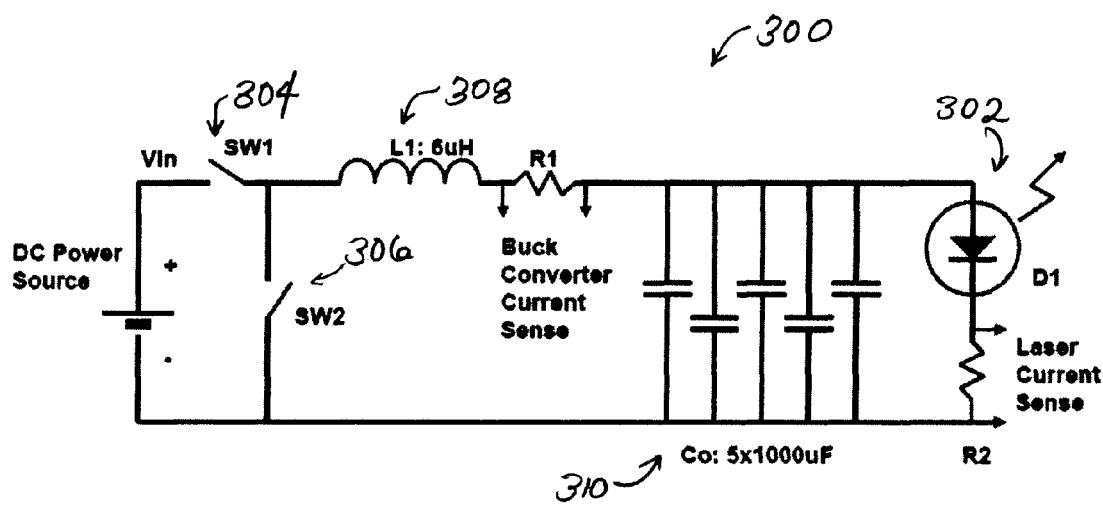

The output capacitance 72 has a relatively small value, for example, about 166 times smaller than in the buck converter of the prior art design shown in FIG. 2. The output capacitance is adapted to absorb relatively large AC current ripple from the inductor 70 that arises from activation of the switches 66, 68. Current ripple is the phenomenon where output current alternatingly rises during the buck on state and falls during the buck off state. The large AC current ripple from inductor 70 is desirable for current mode control. Current mode control may include control of peak current or average current. Peak current mode control generally provides the fastest response and bandwidth. The relatively small value of the output capacitance, which may be 30 microfarads in some embodiments, speeds up the system response and provides cost benefits since relatively inexpensive ceramic capacitors may be used as opposed of electrolytic bulk capacitors used in prior art designs that are needed to provide relatively large output capacitance.

Still referring to FIG. 10, a current controller 69 is shown in block diagram form and operatively connected to the series and parallel switches 66, 68. The current controller can include one or more digital microcontrollers. The current controller is adapted to activate and deactivate the switches 66, 68 to control the level of current provided to the laser 64. A sense resistor 71 between the parallel switch 68 and the output capacitance 72 may be implemented to provide a feedback signal to the current controller 69 to allow for accurate adjustment of the output current of the buck converter 62.

As previously mentioned, a large output capacitance, such as 5000 microfarads shown in FIG. 2, is used in prior art designs so that there is very small voltage ripple, which ensures almost constant load to the laser. For the embodiment of the present invention shown of FIG. 9, large AC current ripple from the buck inductor 70 is desirable so current mode control operates reliably. AC ripple in the output current of the buck converter 62 also occurs when an output switch 76, also referred to as a "chopper," is activated (turned on, or placed in a closed state). The output switch 76 can be a MOSFET, bipolar transistor, or other semiconductor device adapted to be electronically controlled to allow for switching rates of up to tens of megahertz. Switching rates include without limitation 10 MHz, 20 MHz, 30 MHz, and 40 MHz. It will be appreciated that other switching rates may be implemented. The output switch 76 is connected across (parallel to) the laser 64 and is used to pulse the current from the buck converter 62. To minimize the AC current ripple to the laser 64, a second inductor 74, referred to as an "output inductor," having a relatively large value is located at the buck converter output. The output inductor 74 is external to the buck topology after the output capacitance 72 and is connected serially to the laser 64 before the output switch 76.

In the illustrated embodiment of FIG. 10, the buck inductor 70 has a value of 1 microhenry, and the output inductor 74 has a value of 10 microhenries. It will be appreciated that other inductor values may be implemented. The output inductor 74 is adapted to isolate the buck current source from the output where the output switch 76 is located. The output inductor 74 has a large inductance value so current ripple is small even when the output is periodically shorted or shunted by the output switch 76. It will be appreciated that the inductance value of output inductor 74 is chosen to allow for small current ripple to the laser, while the inductance value of the buck inductor 70 is chosen to allow for large current ripple and, thereby, allow for reliable current mode control in the buck converter 62.

Activating (closing or turning on) the output switch 76 shunts the laser 64 and, thereby, effectively ensures zero current to the laser. Accordingly, the speed of the current pulsing does not depend on circuit values, but is fundamentally limited by the stray inductance in the loop between the output switch 76 and the laser diode 64. The stray inductance in the loop can be made quite small using methods known in the art, thereby ensuring very fast switching of the current in the laser. The frequency of the pulses can, therefore, also be very fast. The output switch 76 allows pulsing at a frequency and any pulse width (duty cycle), as shown in FIG. 10*a*. User input controls, such as a dial or switch, coupled to the controller 69 may allow the user to adjust the light intensity or color or both, as desired, by causing a change in duty cycle or pulse frequency or both.

Figure 3:
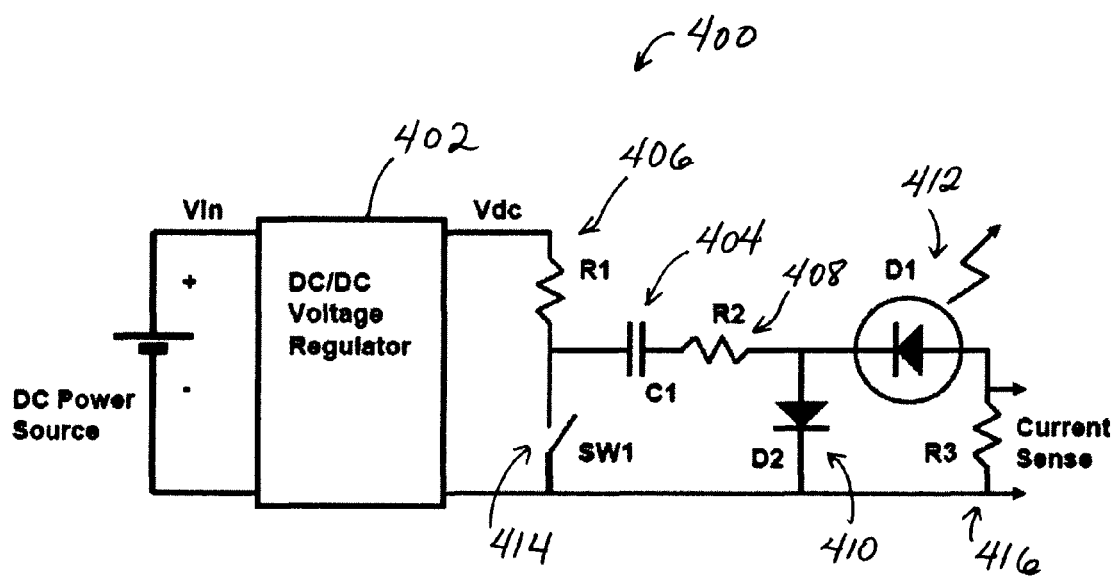
Figure 10B:
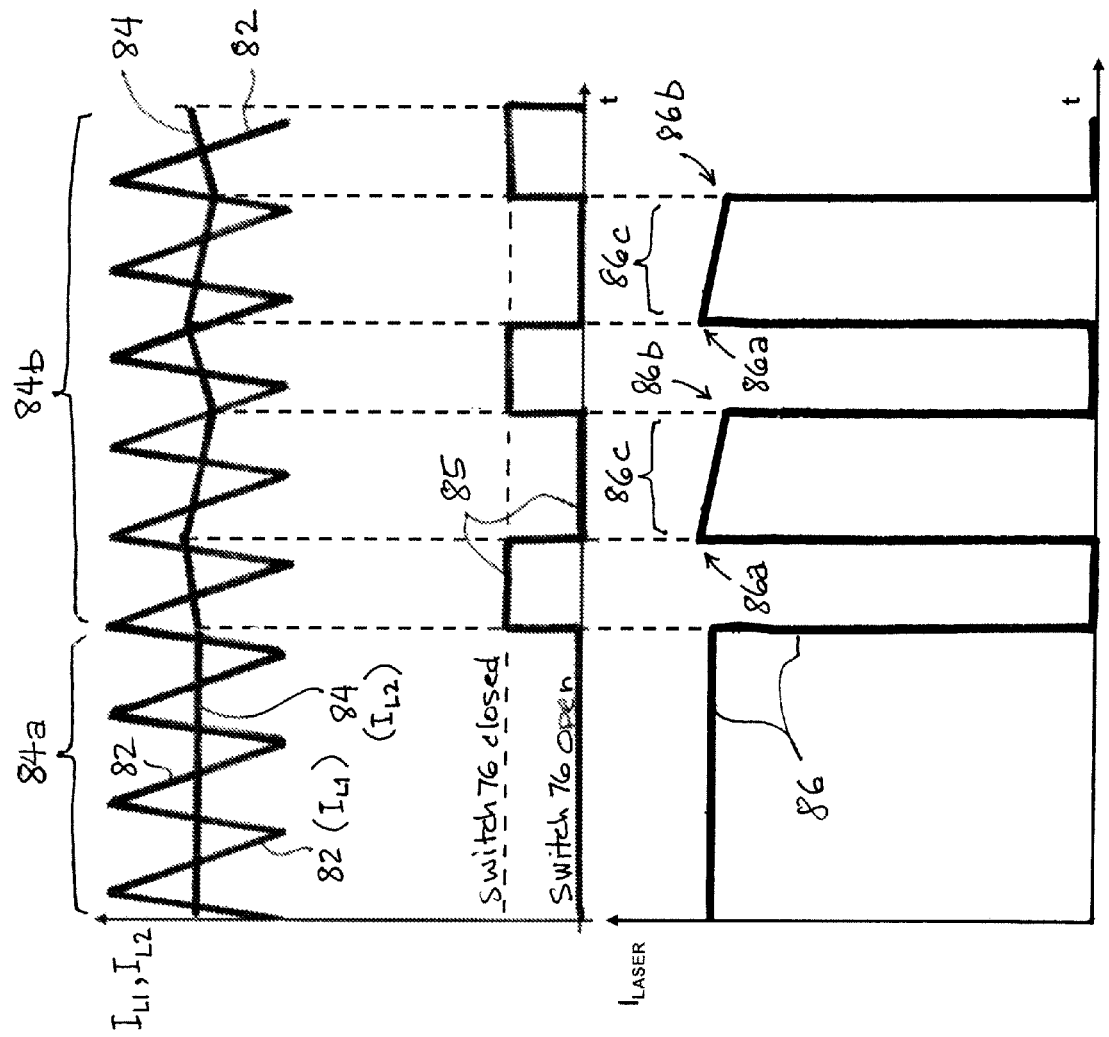
FIG. 10*b* is a plot of the current to a laser provided by the drive circuit of FIG. 10 in relation to current through the inductors of the drive circuit.

As the buck current sense resistor 71 is effectively in series with the buck inductor (L1) 70, controlling current in the sense resistor controls current to L1. The capacitors 72 can conduct only AC ripple, whereas the output inductor (L2) 74 has the same DC component or average current as L1, but L2 has zero current ripple (when switch (SW3) 76 is constantly off (open)) or very small current ripple (when SW3 is pulsing on/off). The difference in current ripple is shown in FIG. 10*b*, where line 82 represents current through L1 and line 84 represents current through L2. Current through L2 is pulsed to the laser 64 when SW3 is open. Segment 84*a* of line 84 shows zero current ripple when SW3 is constantly open, and segment 84*b* of line 84 shows very low current ripple as a result of SW3 pulsing. Line 85 in FIG. 3 represents the open/close state of SW3. Line 86 in FIG. 3 represents the pulsed current to the laser 64. It will be appreciated that the driver 60 is capable of providing current 86 to the laser which is constant with no ripple (corresponding line segment 84*a*) and which is pulsed with very little ripple (corresponding to line segment 84*b*).

Current mode control such as peak current mode or average current mode control can be used to control the current in L1, while current ripple in L1 does not affect or increase current ripple in L2. In particular, peak current mode control provides very fast reaction, but it requires significant current ripple in L1, as compared to small current ripple desired for supplying the laser. The independence of current ripple in L1 (large for peak current mode control, for example), and current ripple in L2 (small for the laser) is an advantage of the present invention.

With continued reference to FIG. 10, a PWM controller 77 is shown in block diagram form and operatively connected to the output switch 76. The PWM controller can include one or more digital microcontrollers which can be separate from or be an integral part of the current controller 69. The PWM controller 77 is configured to activate and deactivate the output switch 76 and to control the frequency at which the output switch 76 activates and deactivates and to control the time duration that the semiconductor is activated and deactivated. The frequency at which the semiconductor activates and deactivates corresponds to the current pulse frequency to the laser. The fraction of time that the semiconductor 56 is deactivated (open state) corresponds to the current duty cycle.

The driver circuit shown in FIG. 10 provides very constant current output to the laser 64 when the output switch 76 (chopper) is inactive (in an open state). When the output switch 76 is inactive, the buck inductor 70 introduces a current with needed DC component but, also, with AC ripple due to switching operation of the buck converter topology (i.e., due to operation of the an upper or series switch 66 and lower or parallel switch 68 of the buck converter 62). As previously mentioned, relatively large current ripple in the buck converter allows for easier and more reliable operation of the current mode control.

Peak current mode control, such as may be performed by the controller 69 of FIG. 10 or other controller connected to the buck topology 62, means that some error amplifier creates feedback signal that comes to one input of a comparator, while another input of the comparator is fed with the sensed current waveform. When the sensed current waveform reaches the provided reference voltage, the comparator switches, resulting in a change of state in the switching power supply topology. The related inductor current is then ramped down, to be switched again, either by a fixed frequency clock waveform or by another comparator (as, for example, in an hysteretic current mode control). Every time there is a comparator in a switching circuit, there is always a question of reliable operation due to the noise of the power stage. Thus, small current ripple in the buck inductor 70 would provide very little slope of the signal, and very little distinction for the comparator to define a switching event. On the other hand, large current ripple in the buck inductor 70 provides much better signal to noise ratio and results in reliable switching operation. Added to the noise problem is input inaccuracy of the comparator resulting from the input offset, drift and other parameters. With a small current ripple, the resulting small amplitude of the sensed current signal generally results in irregular and non reliable switching performance. Thus, a relatively large current ripple in the buck inductor 70 is desired to allow for reliable current mode control.

The AC current ripple in the buck inductor 70 is effectively filtered out by the second order filter formed by the output capacitance 72 and the output inductor 76. The second order filter introduces attenuation of 40 dB/decade starting from the corner frequency. The corner frequency of 30 microfarads with 10 microhenries is around 29 kHz, which is a significantly lower than the switching frequency of the buck converter 62, which ensures good attenuation of the current ripple at and above the switching frequency. In contrast, the prior art design of FIG. 2 has only its output capacitance 310 to attenuate AC current ripple in the buck converter, which is essentially a single pole arrangement associated with attenuation of only 20 dB/decade.

In FIG. 10, the absence of capacitance across the laser diode after the output switch 76 means that the output switch 76, advantageously, does not discharge any capacitance during pulsing. As such, switching losses are dramatically reduced as compared to prior art designs and the speed of the rise and fall of the current in the laser is very high so the waveform of the pulsed current is very close to an ideal square wave. As shown in FIG. 10*b*, the square waveform of the pulses results from there being virtually no or very little difference in value between the beginning 86*a* and the end 86*b* of the current pulse 86*c* due to the low amount of current ripple through the output inductor (line 84). As shown in FIGS. 10*a* and 10*b*, the pulses 86*c* are not exponential discharges which characterize the pulses shown in FIG. 3*a* for the prior art driver 400.

Applicant has found that with the output inductor 74 removed from the circuit of FIG. 10, peak mode control or hysteretic current control will suffer greatly in terms of noise and accuracy, since the ripple in the buck inductor 70 will have to be very small to achieve the desired current ripple specification for a laser, when the output switch 76 shorts the buck converter output for appropriate PWM of the laser. Also, activation of the output switch 76 affects the current ripple by changing the slew rate in the buck inductor 74, making any current control very difficult. With the output inductor 74 in place, as shown in FIG. 10, large current ripple in the buck inductor 70 is supported, making current mode control operate reliable. The relatively small value of the output capacitance 72 creates a "voltage source," so the slew rate in the buck inductor 70 is largely unaffected by activation of the output switch 76. As previously mentioned, the relatively large inductance value of the output inductor 74 isolates the buck current source from the output where the output switch 76 is located.

The lower current ripple at the output inductor 74 is due to its relatively large inductance value and the fact that the voltage at the output of the buck inductor 70 is averaged to a much smaller voltage than at the input of the buck converter. The following non-limiting example is illustrative. The solid state laser 64 can have a voltage of approximately 4 volts at load current of 50 amps, and the current delivered to the laser is pulsed by the output switch 76 at high frequency with a 50% duty cycle. When the output switch 76 is turned on (closed state), the laser 64 is shorted and the electrical current that was going to the laser is routed elsewhere. Thus, the average voltage across the laser would be 2 volts, which is derived from the quantity (4 volts×50%)+(0 volts×50%). Stated another way, the voltage across the laser is 4 volts at half the time and 0 volts the rest of the time, giving a time averaged voltage across the laser of 2 volts. Since inductors in general function as a short at DC and effectively average or filter the voltage, the input of the output inductor 74 (at node 78 opposite the laser 64) will have approximately a constant 2 volts. Since the laser 64 has a voltage of 4 volts when conducting the current, the output of the output inductor 74 (at node 80) will have 4 volts when the output switch 76 is open and a 0 volts when the output switch 76 is closed. Since the input of the output inductor 76 (at node 78) has a nearly constant 2 volts, the output inductor 74 effectively has applied to it 2 volts (4 minus 2) of one polarity (when the output switch 76 is open) and 2 volts (0 minus 2) of the opposite polarity (when the output switch 76 is closed). As applied voltage across an inductor for a given time defines its current slew rate, then for similar timing intervals, the inductor with lower voltages applied across it will have similarly smaller current ripple. The applied voltage of 2 volts across the output inductor 74 is relatively small, as compared, for example, to the 12 volt input for the buck converter Vin in this particular example, so the current ripple of the output inductor will be correspondingly be small, which is desirable for optimal operation of the laser 64.

The circuit values for the above-described laser driver circuit (e.g., 4 volt laser driver, 12 volt buck converter input, etc.) are exemplary and are not intended to limit the scope of the invention. The present invention encompasses other circuit values. It will be appreciated that the above-described advantages can be obtained with other circuit values.

The current controller 69 and the PWM controller 77 of FIG. 10 allow for simultaneous and independent adjustment of three parameters of the current to the laser 64, namely level of current, pulse frequency, and pulse width (or duty cycle). Adjustment of these parameters allows for adjustment of the output intensity of the laser.

Figure 11:
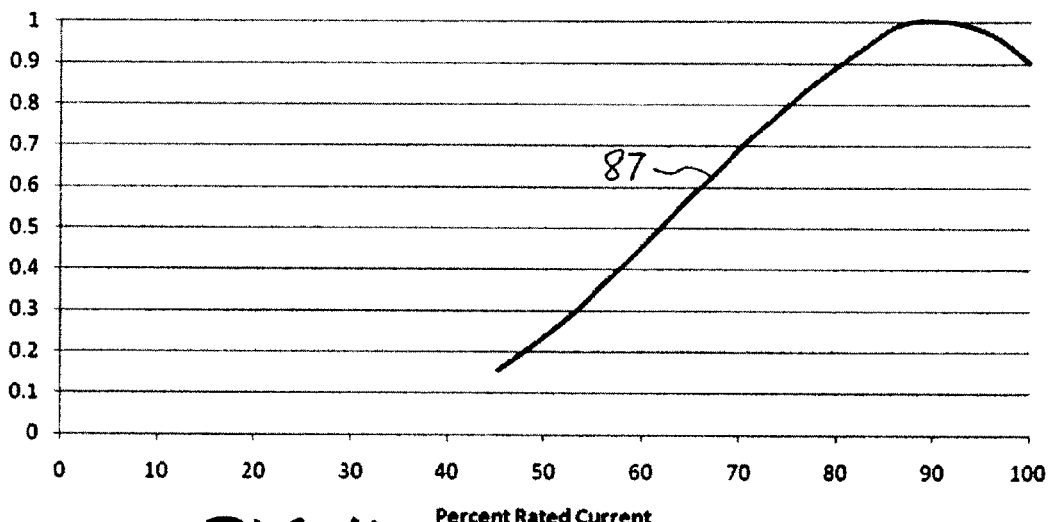
FIG. 11 is a plot of output power of a solid state laser as a function of percentage of rated current to the laser.
Figure 12:
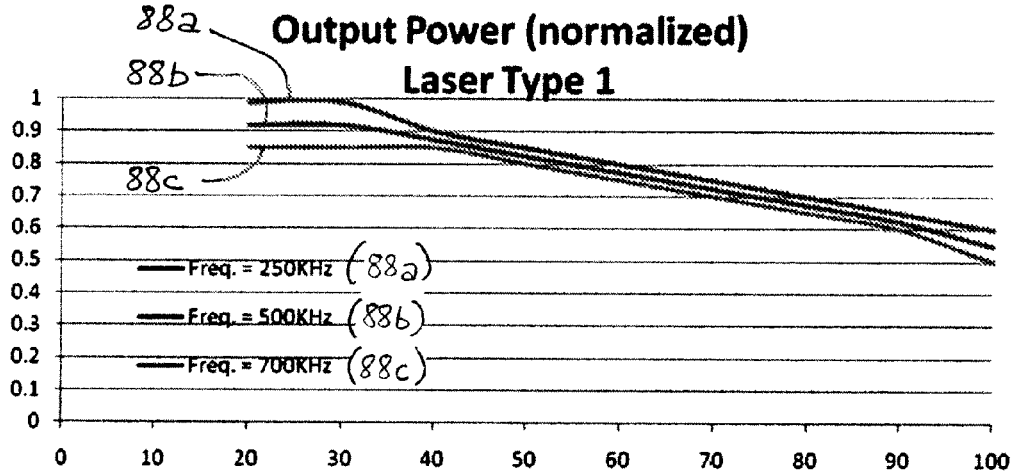
FIGS. 12 and 13 are plots of output power of different solid state lasers as a function of pulse frequency and duty cycle of the current to the laser.
Figure 13:
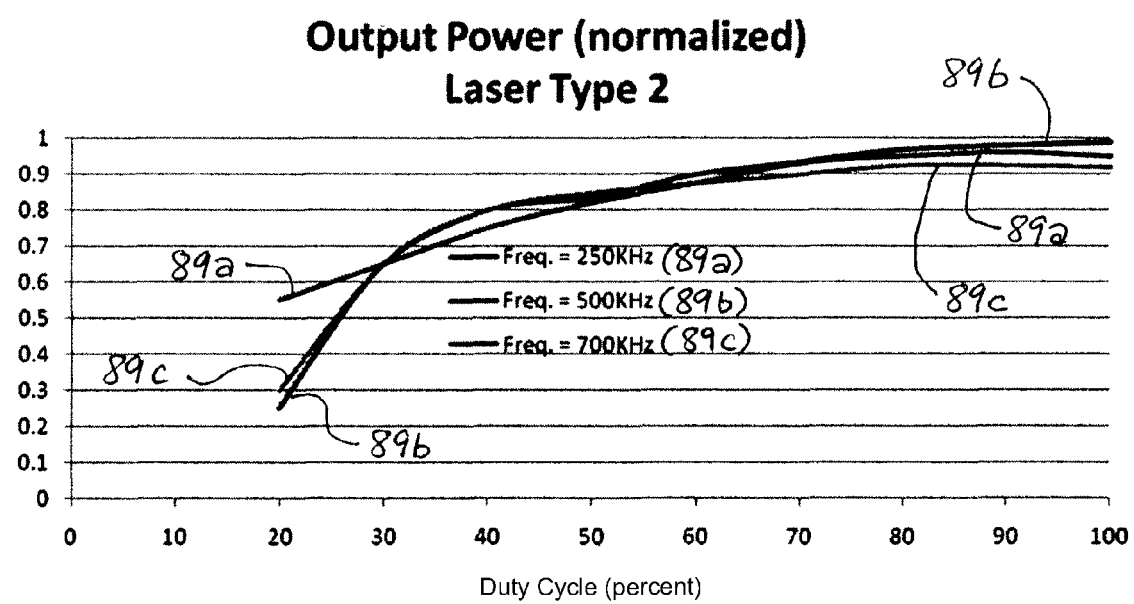

FIGS. 11-13 show efficiency curves for different lasers. In FIG. 11, the vertical axis shows normalized output power from a solid state laser, where 1.0 on the vertical axis indicates maximum output power. The horizontal axis shows the current level to the laser from the driver in terms of percentage of rated current, where 100% on the horizontal axis indicates the amount of current at which the laser is rated. Line 87 shows that efficiency (output power divided by input power) for the particular solid state laser peaks between about 88% and 92% of rated current. The driver may be configured to allow controlled adjustment of the current to the laser in a predetermined band of current level near or around the peak to allow for a desired variation in laser output intensity or power while maintaining optimal output efficiency.

In FIGS. 12 and 13, the vertical axis shows normalized output power from different solid state lasers, where 1.0 on the vertical axis indicates maximum output power. The horizontal axis shows the duty cycle of pulsed current from a driver to the solid state laser. In FIG. 12, lines 88*a*, 88*b*, and 88*c* represent the relationship between output power and duty cycle for pulse frequencies of 250 kHz, 500 kHz, and 700 kHz, respectively, for a first type of solid state laser. In FIG. 13, lines 89*a*, 89*b*, and 89*c* represent the relationship between output power and duty cycle for pulse frequencies of 250 kHz, 500 kHz, and 700 kHz, respectively, for a second type of solid state laser.

For the first type of laser (FIG. 12), output efficiency is greatest with a 250 kHz pulse frequency (line 88*a*) and with a duty cycle between about 20% and 30%. A driver connected to the first type of laser may be configured to provide pulsed current at 250 kHz and allow controlled adjustment of the duty cycle in predetermined band near or around the peak to allow for a desired variation in laser output intensity or power while maintaining optimal output efficiency.

For the second type of laser (FIG. 13), no single pulse frequency provides the greatest efficiency over all duty cycles. At duty cycles above 60%, a pulse frequency at or around 500 kHz provides the greatest efficiency. A driver connected to the second type of laser may be configured to provide pulsed current at 500 kHz when allowing controlled adjustment of the duty cycle above 60%. In this manner, a desired variation in laser output intensity or power can be performed while maintaining optimal output efficiency.

In some embodiments, a light source assembly may include multiple drivers, each connected to a different laser. The drivers may be configured to allow for controlled adjustment over different predetermined bands of current level. The drivers may be configured to provide pulsed current at different selected frequencies from each other. The drivers may also be configured allow for controlled adjustment of duty cycle in different bands. The current level bands, pulse frequencies, duty cycle bands for each driver may be selected based on the individual efficiency curves or characteristics of the laser devices.

Figure 14:
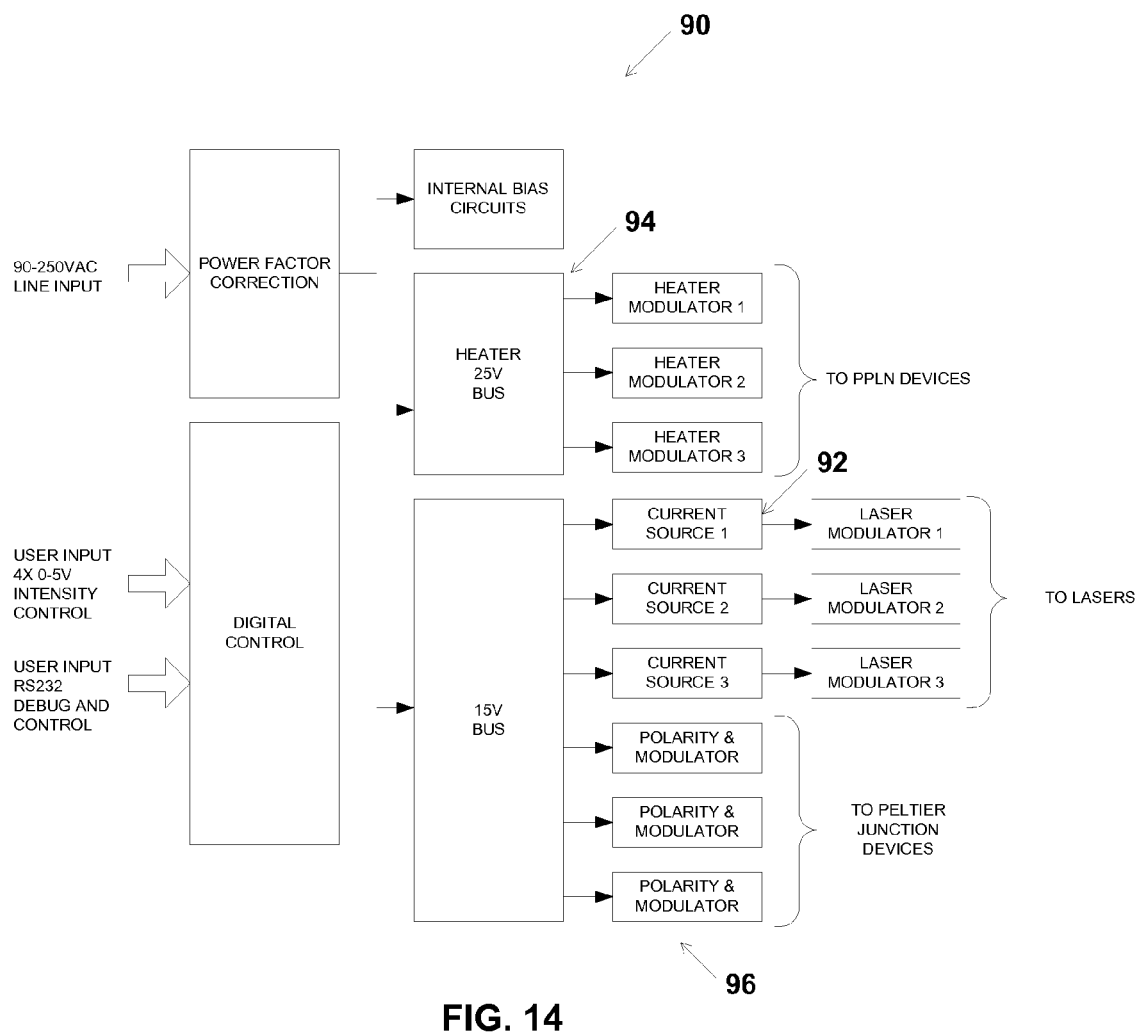
FIG. 14 is a block diagram of a power supply for a light source assembly, showing separate current sources for lasers, for PPLN devices for the lasers, and for cooling/heating devices thermally coupled to cases for the lasers.

In some embodiments, a light source assembly, such as shown in FIG. 4, may include a power supply 90 that is a triple current source, as shown in FIG. 14. A first current source 92 of the power supply 90 provides three separate sources of current for a red laser, a blue laser, and a green laser. A second current source 94 of the power supply 90 provides three separate sources of current to a respective heater modulator 96 connected to a PPLN (periodically poled lithium niobate) crystal for each laser. The PPLN crystals are used to double the spectrum frequency of the light output of the lasers. The device that contains the PPLN crystal, referred to as a PPLN device, operates only over a very narrow temperature range, so its temperature must be monitored and precisely controlled. Temperature control is carried out by varying or modulating the output of the second current source 94, which in turn, varies the heat delivered to the PPLN device. A third current source 96 allows for control of the case temperature of the individual lasers. The lasers must be run at a precise temperature to achieve maximum efficiency. The third current source 96 provides power to a peltier junction device that is thermally coupled to the case of the laser. Varying the current direction and magnitude through the peltier junction device will control whether it heats or cools and control the amount of heating or cooling. In this way, the case of the laser can be maintained at a desired, constant temperature regardless of the ambient temperature.

While several particular forms of the invention have been illustrated and described, it will also be apparent that various modifications can be made without departing from the scope of the invention. For example, the endoscope can be replaced with another device for delivering light from a remote source, such as may be used in a variety of industrial, commercial, and medical applications. In addition to endoscopic applications, various aspects of the present invention are applicable to ophthalmic, laparoscopic, minimally invasive, and open surgical procedures. It is also contemplated that various combinations or subcombinations of the specific features and aspects of the disclosed embodiments can be combined with or substituted for one another in order to form varying modes of the invention. For example, a combination of lasers and LEDs may be implemented within the same light source assembly to provide a desired spectrum of visible and non-visible radiation. Accordingly, it is not intended that the invention be limited, except as by the appended claims.

What is claimed is:

1. A light emitting system comprising: a voltage source; at least one solid state light emitting device adapted to receive output current and emit light; a semiconductor switch electrically connected in parallel to the light emitting device, the switch adapted to periodically activate and deactivate the light emitting device by providing a short across the light emitting device at a pulse frequency and a pulse width to provide a square wave current to the at least one solid state light emitting device; a first inductor that operates as part of a converter, wherein the first inductor is in series with the voltage source and the light emitting device, the converter outputting a current; a second, current source output inductor that receives and filters the output of the converter to reduce current ripple in the current provided by the converter, wherein the second current source output inductor is positioned in series with and between the first inductor and the at least one solid state light emitting device, wherein an output of the second inductor is provided to the semiconductor switch and solid state light emitting device; and an output capacitor positioned between the first inductor and the second, current source output inductor at an output of the first inductor.

2. The system of claim 1, wherein the converter comprises a buck topology that includes a series buck switch, a parallel buck switch, and a buck inductor comprising the first inductor, wherein the buck switches are transistor devices, and wherein the system further comprises a controller, wherein the controller controls activation and deactivation of the buck switches in order to adjust the peak level, the average level, or both the peak and average levels of the output current.

3. The system of claim 2, wherein the output inductor is configured to provide a current that goes to the light emitting device when the semiconductor switch is activated to an open state and that is diverted away from the light emitting device and runs through the semiconductor switch when the semiconductor switch is deactivated to a closed state.

4. The system of claim 2, wherein the controller controls activation and deactivation of the semiconductor switch in order to adjust the pulse frequency and the pulse width.

5. The system of claim 2, wherein current ripple is generated by the buck switches and the semiconductor switch, and wherein the output capacitor and the output inductor form a filter configured to filter the current ripple that would otherwise go to the light emitting device.

6. The system of claim 1, wherein the system comprises a plurality of solid state lasers, each one of the solid state lasers outputting light that is mixed together in an output optical fiber.

7. The system of claim 6, further comprising an endoscope optically coupled to a distal end of the output optical fiber.

8. The system of claim 6, wherein the plurality of solid state lasers includes a first laser configured to output red light, a second laser configured to output green light, and a third laser configured to output blue light.

9. The system of claim 6, further comprising a plurality of supply optical fibers, each of the supply optical fibers having a proximal end optically coupled to a different one of the plurality of solid state lasers and a distal end out of which laser light is emitted, the distal ends fused to a proximal end of the output optical fiber which receives the emitted light.

10. The system of claim 6, further comprising:
a plurality of supply optical fibers, each of the supply optical fibers having a proximal end optically coupled to a different one of the plurality of solid state lasers and a distal end out of which laser light is emitted; and
a lens adapted to focus the light emitted from the distal ends of the supply optical fibers onto the proximal end of the output optical fiber.

11. The system of claim 6, wherein a proximal end of the output optical fiber receives the light outputted from each one of the solid state lasers, and the output optical fiber is coiled to produce internal reflections that mixes the received light.

12. The system of claim 1, wherein the solid state light emitting device is a laser diode.

13. The system of claim 1, wherein a switching rate of the semiconductor switch is at least 10 MHz.

14. A method of emitting light, the method comprising: providing electrical current to a plurality of solid state light emitting devices that produce light at a different spectrum from each other, the provided current having a peak or average level and a pulse waveform defined by a pulse frequency and duty cycle, wherein a first inductor operates as part of a converter, and wherein the first inductor is in series with a voltage source and at least one of the plurality of solid state light emitting devices; wherein a semiconductor switch is electrically connected in parallel to the at least one light emitting device, the semiconductor switch adapted to periodically activate and deactivate the at least one light emitting device by providing a short across the at least one light emitting device; mixing the light produced by each one of the light emitting devices; adjusting the intensity of the light produced by the at least one of the light emitting devices, the adjusting including at least one of changing the peak or average level, the pulse frequency, and the duty cycle of the current provided to the at least one of the light emitting devices; and filtering current ripple induced by the converter, wherein the filtering is performed using, at least a second, current source output inductor that receives and filters the output of the converter to reduce current ripple in a current provided by the converter, and an output capacitor positioned between the first inductor and the second, current source output inductor at an output of the first inductor; wherein the second current source output inductor is positioned in series with and between the first inductor and the at least one of the plurality of solid state light emitting devices, wherein an output of the second inductor is provided to the semiconductor switch and solid state light emitting device.

15. The method of claim 14, wherein adjusting the intensity includes changing the peak or average level and the duty cycle.

16. The method of claim 14, wherein adjusting the intensity includes changing the pulse frequency or pulse width through control of the semiconductor switch.

17. The method of claim 14, wherein the converter comprises a buck topology that includes a series buck switch, a parallel buck switch, and a buck inductor comprising the first inductor, wherein the buck topology further includes a power source electrically connected to the series buck switch and the buck switches are transistor devices.

18. The method of claim 17, wherein the filtering is performed at least by a filter comprising the output capacitor and the output inductor at the output of the buck topology.

19. The method of claim 14, wherein the light emitting devices are laser devices, and wherein the laser devices are laser diodes.

* * * * *